United States Patent [19]

Freytag

[11] 4,397,877

[45] Aug. 9, 1983

[54] HEAT TREATMENT OF ACTIVE DRIED YEAST AND PRODUCT THEREOF

[75] Inventor: Arthur H. Freytag, Longmont, Colo.

[73] Assignee: The Great Western Sugar Company, Denver, Colo.

[21] Appl. No.: 213,362

[22] Filed: Dec. 5, 1980

[51] Int. Cl.³ .......................... C12G 1/00; C12N 1/18; C12N 1/16; C12P 7/06

[52] U.S. Cl. ........................................ 426/11; 426/15; 426/62; 435/161; 435/255; 435/256

[58] Field of Search ....................... 426/11, 15, 60, 62, 426/466, 520, 61; 435/161, 255, 256, 260

[56] References Cited

U.S. PATENT DOCUMENTS

| | | | |
|---|---|---|---|
| 3,615,685 | 10/1971 | Fantozzi et al. | 435/260 |
| 3,780,181 | 12/1973 | Trevelyan | 426/18 |
| 3,962,467 | 6/1976 | Burrows | 435/255 |
| 4,021,579 | 5/1977 | Barrett | 426/11 |

OTHER PUBLICATIONS

Cysewski, G. R. et al., "Rapid Ethanol Fermentations Using Vacuum and Cell Recycle", Biotechnology & Bioengineering, vol. 14, pp. 1125–1143.

*Primary Examiner*—Raymond N. Jones
*Assistant Examiner*—Elizabeth J. Curtin
*Attorney, Agent, or Firm*—Bruce G. Klaas; Jerry W. Berkstresser; Donald W. Margolis

[57] ABSTRACT

Active dried yeast is treated to beneficiate subsequent fermentation activity and/or fermentation products of the yeast and to produce a beneficiated active yeast product by heating the dried yeast to a temperature of about 30° to about 60° C. for at least about 2 hours prior to utilization of the yeast in a fermentation process.

14 Claims, No Drawings to cost of the production process.

HEAT TREATMENT OF ACTIVE DRIED YEAST AND PRODUCT THEREOF

BACKGROUND AND SUMMARY OF THE INVENTION

This invention relates to methods of beneficiating the fermentation activity and/or fermentation products of yeast and to a beneficiated yeast product. More particularly, this invention relates to a method of treating active yeast having a relatively low moisture content by heating the yeast prior to utilization of the yeast in a fermentation process, and to the product of the method.

The present worldwide energy shortage has placed a large emphasis on the need to develop potential energy sources other than depletable oil, gas and coal reserves. One potential alternative energy source which has received substantial attention is the production of alcohol, such as ethyl alcohol, from renewable carbohydrate sources, such as corn, grains and other vegetable matter.

In one general approach to the production of ethyl alcohol, a carbohydrate source is subjected to the biological action of suitable yeast organisms to convert at least a portion of the carbohydrates to ethyl alcohol in a process generally referred to as fermentation. After completion of carbohydrate conversion to ethyl alcohol, the produced alcohol is typically recovered from a fermentation mixture by distillation, and then subsequently utilized, such as for a fuel source, as a chemical reagent or solvent, in a consumable alcoholic beverage, or for other purposes. In the past, much of the effects to increase the efficiency of alcohol production from biological or fermentation processes have been directed to maximizing still efficiency or to isolating particular yeast strains which exhibit desired properties in the fermentation process.

There is still a substantial need, however, for new methods or processes which may increase the efficiency of fermentation processes and thereby reduce the costs of alcohol production.

In accordance with the present invention, it has been unexpectedly determined that the fermentation activity of dried yeast, and therefore the efficiency of a fermentation process, can be significantly enhanced by heating a previously dried, active yeast prior to incorporation of the dried yeast into a fermentation mixture. Yeast suitable for use in connection with the invention include active dry yeast which has been produced by known yeast drying processes. Dried yeast is typically produced by innoculating a nutritive medium with active yeast cells, allowing the yeast cells to grow and multiply, recovering a larger volume of yeast cells from the nutritive medium and then drying the recovered yeast in order to obtain a yeast product that can be economically transported and stored. To preserve the activity of yeast during relatively long storage periods, it is a common practice to reduce the moisture content of the recovered yeast prior to packaging for transportation, storage and/or sale. Thus, it is a common practice to compress the recovered yeast, or to subject the yeast to various drying processes, to reduce the moisture content of the yeast to, for example, about 5 to about 20 percent by weight. In typical yeast drying processes, yeast recovered from a liquid medium is subjected to heated air to reduce the moisture content of the yeast to a desired level. It has been generally recognized, however, that the yeast drying temperatures must be carefully controlled in order not to reduce the activity of the dried yeast. In order to avoid the problems of yeast deactivation, yeast drying processes have generally been limited to temperatures of 30° to 40° C. For example, U.S. Pat. Nos. 1,420,558, 1,643,047, 1,859,250 and 2,111,201 relate to such processes. In general, it has been thought that high temperatures must be avoided in order to maintain dry yeast activity.

In order to decrease drying time, it has been suggested in U.S. Pat. No. 3,962,467 of Burrows that yeast may be dried in a fluidized bed in a process which raises the yeast temperature above 50° C. at the end of the drying process. It is recognized in the Burrows patent, however, that the use of yeast temperatures above 50° C. has to be adopted with some degree of caution and if the yeast is maintained at an undesirably high temperature for too long its activity can be seriously damaged. The Burrows patent teaches that the yeast temperature must be above 50° C. For less than 45 minutes, usually less than 30 minutes and most preferably only for the last 15 or 20 minutes of the drying operation. Thus, the Burrows patent confirms the generally held belief that yeast temperatures and drying times must be carefully limited to avoid yeast damage and deactivation or activity reduction.

In view of the care which must be exercised when drying yeast, it is even more surprising and unexpected that dried yeast can be beneficiated according to the process of the invention by heating the dried yeast to temperatures of about 30° to about 60° C. for at least about 2 hours prior to utilization of the yeast in a fermentation process. Yeast treatment according to the invention has been found to enhance the fermentation activity of the yeast and/or to beneficially alter the products of a fermentation process in which the beneficiated yeast is employed.

DESCRIPTION OF ILLUSTRATIVE EMBODIMENTS OF THE INVENTION

According to the method of the invention, conventionally dried yeast is treated prior to utilization of the yeast in a fermentation process by heating the yeast to a temperature of about 30° to about 60° C. for a period of at least about 2 hours to produce a beneficiated dried yeast product.

As used herein, the term "dried yeast" means active yeast having a moisture content less than about 20%, more preferably less than about 15%, and most preferably less than about 10% by weight. It is contemplated that the yeast may be any commercially available active dried or powdered yeast, or any other yeast having the desired moisture content.

It has been determined that the herein described heat treatment of dried yeast results in beneficiation of the yeast by enhancing its fermentation activity when subsequently employed in a fermentation process. It has been further surprisingly found that when the desired end product of the fermentation process is an alcoholic beverage, such as wine, utilization of yeast which has been heat treated according to the invention results in beneficiation of the resulting beverage by altering the color, flavor, aroma and/or other characteristic properties of the beverage to produce qualities similar to that of natural aging. Thus, practice of the invention can result in a decrease in the normal fermentation time of an ethyl alcohol production process and/or a beneficial reduction in the normal aging time of an alcoholic beverage production process.

Dried yeast may be treated according to the invention by heating the yeast in a static oven, in a forced air oven, on a fluidized bed, or by other suitable means employing a dry heating source.

In order to obtain the beneficiation of the present invention, conventially dried yeast is heated to a yeast temperature of about 30° to about 60° C., more preferably about 35° to about 55° C., and most preferably about 45° to about 55° C., for a period of at least about 2 hours, more preferably about 3 to about 30 hours and most preferably about 4 to about 20 hours. After treatment, the treated yeast may be employed in a fermentation mixture of a fermentation process to obtain the desired results. It has been further determined that yeast which has been treated according to the invention maintains its beneficiated properties for substantial periods of time after treatment, and may therefor be stored, for example up to six months or longer, prior to utilization in a fermentation process.

The heat treatment disclosed herein may be practiced alone, or may be practiced in connection with subjecting the fermentation mixture of a fermentation process to less than atmospheric pressures, as disclosed and claimed in my copending U.S. patent application Ser. No. 206,959 filed Nov. 14, 1980, the disclosure of which is hereby incorporated herein by reference. When practiced in connection with carrying out fermentation at reduced pressures, the desired increase in fermentation activity of the yeast and/or the beneficiation of the fermentation products can be even further enhanced.

The foregoing may be better understood in connection with the following illustrative examples:

EXAMPLE I

Commercially available, dried bakers yeast (Red Star or Fleischman brand), obtained in sealed foil envelopes, is evenly spread across the bottom of a 50 ml beaker. The yeast is placed in a Thelco Precision Model 28 forced air oven which has been preheated to a temperature of 60° C. The yeast is heated in the oven with occasional stirring during the heating period. After a period of 20 hours, the yeast is removed from the oven and allowed to cool to room temperature.

Ten fermentation mixtures are prepared by combining in each 100 grams of molasses and 200 grams of distilled water. Five of the fermentation mixtures are each inoculated with 3 grams of heat treated yeast while the remaining fermentation mixtures are each inoculated with 3 grams of the same type of yeast which has not been treated according to the invention. The pH of each fermentation mixture is adjusted to 5.0 with HCl. The mixtures are allowed to undergo fermentation for a period of 24 hours at the temperatures shown in Table I:

TABLE I

| Run No. | Yeast | Fermentation Temperature (°C.) |
|---|---|---|
| 1 | Untreated | 21.1 |
| 2 | Treated | 21.1 |
| 3 | Untreated | 23.9 |
| 4 | Treated | 23.9 |
| 5 | Untreated | 26.7 |
| 6 | Treated | 26.7 |
| 7 | Untreated | 35.0 |
| 8 | Treated | 35.0 |
| 9 | Untreated | 36.7 |
| 10 | Treated | 36.7 |

The specific gravities of the mixtures during fermentation are shown in Table II:

TABLE II

| Time From Start of Fermentation (hrs) | Specific Gravity Run No. | | | | | | | | | |
|---|---|---|---|---|---|---|---|---|---|---|
| | 1 | 2 | 3 | 4 | 5 | 6 | 7 | 8 | 9 | 10 |
| 2 | 1.104 | 1.104 | 1.100 | 1.100 | 1.103 | 1.104 | 1.100 | 1.098 | 1.100 | 1.098 |
| 4 | 1.104 | 1.102 | 1.100 | 1.096 | 1.102 | 1.100 | 1.099 | 1.092 | 1.096 | 1.090 |
| 6 | 1.104 | 1.102 | 1.100 | 1.094 | 1.100 | 1.094 | 1.096 | 1.084 | 1.086 | 1.080 |
| 8 | 1.102 | 1.098 | 1.101 | 1.092 | 1.093 | 1.090 | 1.094 | 1.083 | 1.080 | 1.074 |
| 12 | 1.096 | 1.090 | 1.096 | 1.080 | 1.083 | 1.070 | 1.080 | 1.066 | 1.062 | 1.054 |
| 24 | 1.072 | 1.066 | 1.072 | 1.048 | 1.036 | 1.030 | 1.044 | 1.036 | 1.040 | 1.034 |

As shown in Table II, the fermentations conducted with treated yeast exhibit a significant acceleration in specific gravity reduction over the fermentations conducted under similar conditions with untreated dried yeast.

After the 24 hour fermentation period, the fermentation mixtures are distilled and ethyl alcohol distillate is recovered and measured. The recovered ethyl alcohol from each fermentation is shown in Table III:

TABLE III

| Fermentation Temp. (°C.) | Recovered Ethyl Alcohol (ml) | |
|---|---|---|
| | Untreated | Treated |
| 21.1 | 4.7 | 6.4 |
| 23.9 | 3.0 | 11.0 |
| 26.7 | 10.0 | 12.5 |
| 35.0 | 8.5 | 13.0 |
| 36.7 | 11.8 | 13.5 |

As shown in Table III, the fermentations conducted with treated yeast exhibit a significant increase in ethyl alcohol production over fermentations conducted under similar conditions with untreated yeast.

EXAMPLE II

In order to demonstrate the effects of heat treatment time on the fermentation activity of dried yeast, the procedure of Example I is repeated by heating samples of the untreated yeast of Example I to a temperature of 60° C. for periods of 2, 5, 10, 20 and 40 hours, respectively. Six fermentation mixtures are prepared by combining in each 100 grams of molasses and 200 grams of distilled water. One of the mixtures is innoculated with 3 grams of untreated yeast, while the remaining mixtures are each innoculated with 3 grams of one of the different heat treated yeast samples. The pH of each fermentation mixture is adjusted to 5.0 with HCL and the mixtures are allowed to undergo fermentation at a temperature of 23° C. for a period of 24 hours. The specific gravities of the mixtures during fermentation are shown in Table IV:

TABLE IV

| Time From Start of Fermentation (hrs) | Specific Gravity | | | | | |
|---|---|---|---|---|---|---|
| | Yeast Treatment Time (hrs) | | | | | |
| | Untreated | 2 | 5 | 10 | 20 | 40 |
| 0 | 1.104 | 1.102 | 1.102 | 1.103 | 1.103 | 1.104 |
| 2 | 1.104 | 1.102 | 1.102 | 1.103 | 1.103 | 1.104 |
| 4 | 1.101 | 1.100 | 1.100 | 1.100 | 1.101 | 1.104 |
| 6 | 1.096 | 1.096 | 1.095 | 1.098 | 1.100 | 1.103 |
| 8 | 1.096 | 1.094 | 1.093 | 1.093 | 1.092 | 1.100 |
| 12 | 1.088 | 1.080 | 1.079 | 1.078 | 1.082 | 1.096 |
| 24 | 1.050 | 1.042 | 1.042 | 1.042 | 1.044 | 1.064 |

After the 24 hour fermentation period, the fermentation mixtures are distilled and the ethyl alcohol produced during fermentation is recovered. The amount of ethyl alcohol recovered from each fermentation mixture is shown in Table V:

TABLE V

| Recovered Ethyl Alcohol (ml) | |
|---|---|
| Yeast Treatment Time (hrs) | Ethyl Alcohol (ml) |
| Untreated | 6.8 |
| 2 | 8.0 |
| 5 | 9.5 |
| 10 | 9.0 |
| 20 | 8.0 |
| 40 | 5.0 |

As shown in Table IV and V, with the exception of yeast treated for a period of 40 hours, the fermentations conducted with heat treated yeast exhibit a significant acceleration in specific gravity reduction and in ethyl alcohol production over the fermentation conducted under similar conditions with untreated dried yeast.

EXAMPLE III

In order to demonostrate the effects of heat treatment temperature on the fermentation activity of dried yeast, the procedure of Example I is repeated by heating samples of the untreated yeast of Example I for a period of 5 hours to temperatures of 32.2, 37.8, 43.3, 48.9, 54.4, 60.0 and 65.6° C., respectively. Eight fermentation mixtures are prepared by combining in each 100 grams of molasses and 200 grams of distilled water. One of the mixtures is innoculated with 3 grams of untreated yeast, while the remaining mixtures are each innoculated with 3 grams of one of the different heat treated yeast samples. The pH of each fermentation mixture is adjusted to 5.0 with HCL and the mixtures are allowed to undergo fermentation at a temperature of 23° C. for a period of 24 hours. The specific gravities of the mixtures during fermentation shown in Table VI:

TABLE VI

| Time From Start of Fermentation (hrs) | Specific Gravity | | | | | | | |
|---|---|---|---|---|---|---|---|---|
| | Yeast Treatment Temperature (°C.) | | | | | | | |
| | Untreated | 32.2 | 37.8 | 43.3 | 48.9 | 54.4 | 60.0 | 65.6 |
| 0 | 1.102 | 1.100 | 1.100 | 1.102 | 1.102 | 1.100 | 1.102 | 1.102 |
| 2 | 1.100 | 1.100 | 1.100 | 1.098 | 1.098 | 1.100 | 1.100 | 1.102 |
| 4 | 1.098 | 1.098 | 1.100 | 1.098 | 1.098 | 1.100 | 1.100 | 1.100 |
| 6 | 1.098 | 1.098 | 1.100 | 1.098 | 1.098 | 1.098 | 1.098 | 1.100 |
| 8 | 1.096 | 1.096 | 1.094 | 1.094 | 1.093 | 1.094 | 1.094 | 1.098 |

TABLE VI-continued

| Time From Start of Fermentation (hrs) | Specific Gravity | | | | | | | |
|---|---|---|---|---|---|---|---|---|
| | Yeast Treatment Temperature (°C.) | | | | | | | |
| | Untreated | 32.2 | 37.8 | 43.3 | 48.9 | 54.4 | 60.0 | 65.6 |
| 12 | 1.083 | 1.082 | 1.082 | 1.084 | 1.080 | 1.080 | 1.084 | 1.092 |
| 24 | 1.040 | 1.034 | 1.034 | 1.032 | 1.032 | 1.034 | 1.036 | 1.040 |

After the 24 hour fermentation period, the fermentation mixtures are distilled and the ethyl alcohol produced during fermentation is recovered. The amount of ethyl alcohol recovered from each fermentation mixture is shown in Table VII:

TABLE VII

| Yeast Treatment Temp. (°C.) | Ethyl Alcohol (ml) |
|---|---|
| Untreated | 8.5 |
| 32.2 | 11.0 |
| 37.8 | 10.1 |
| 43.3 | 11.2 |
| 48.9 | 11.0 |
| 54.4 | 11.6 |
| 60.0 | 9.5 |
| 65.6 | 8.0 |

As shown in Tables VI and VII, with the exception of yeast treated at a temperature of 65.6° C., the fermentations conducted with heat treated yeast again exhibit a significant acceleration in specific gravity reduction and in ethyl alcohol production over the fermentation conducted under similar conditions with untreated dried yeast.

EXAMPLE IV 2740 lbs of newly harvested cabernet sauvignon grapes are stemmed and crushed to form a must, and the must is distributed equally into 55 gallon stainless steel drums, each drum containing about 35 gallons of grape must.

Two 20 g. samples of Red Star pasteur champagne (all purpose) yeast are initially treated by heating the samples to a temperature of 54.4° C. for a period of 5 hours. Six separate yeast starter innoculums are prepared by combining in each 100 ml of distilled water, 100 ml of juice from the crushed grapes and 20 g of Red Star pasteur champagne (all purpose) yeast, two of the innoculums being prepared from the previously heat treated yeast samples. The yeast starter innoculums are allowed to stand for a period of 1 hour and are then each mixed into the grape must in one of the separate drums, with the grape must in four of the drums (designated as Runs 1, 2, 4 and 5) containing untreated yeast and with the grape must in two of the drums (designated as Runs 3 and 4) containing heat treated yeast.

Immediately after innoculation of the musts, the drums of Runs 4, 5 and 6 are sealed and connected to separate vacuum pumps. The drums of Runs 1, 2 and 3 are stoppered with a cotton plug. The grapes musts of Runs 1, 2 and 3 are allowed to undergo fermentation at a temperature of 17.2° C. and at atmosphere pressure. The grape musts of Runs 4 and 5 are allowed to undergo fermentation at a temperature of 17.2° C. and at a reduced pressure of 15" Hg. The grape must of Run 6 is allowed to undergo fermentation at a temperature of 17.2° C. and at a reduced pressure of 25" Hg.

Periodically, 250 ml samples are removed from each fermenting must, and are analyzed for dissolved solids by Brix hydrometer, which approximates the percentage of dissolved sugar in each must. The results of these measurements are shown in Table VIII:

TABLE VIII

| Time From Start of Fermentation (days) | °Brix | | | | | |
|---|---|---|---|---|---|---|
| | Run 1 (Control) | Run 2 (Control) | Run 3 (Treated) | Run 4 (Treated/ Vacuum) | Run 5 (15" Vacuum) | Run 6 (25" Vacuum) |
| 0 | 22.7 | 22.7 | 22.7 | 22.7 | 22.7 | 22.7 |
| 2 | 17.0 | 17.0 | 17.0 | 16.4 | 14.4 | 14.3 |
| 3 | 12.0 | 12.2 | 12.0 | 10.0 | 5.4 | 7.5 |
| 4 | 5.8 | 6.1 | 5.5 | 4.9 | 2.2 | 3.9 |
| 5 | 2.2 | 2.4 | 2.0 | 1.5 | 1.5 | 1.5 |

On the fifth day following the start of fermentation, samples are removed from each must and are presented to a professional taste panel for sensory evaluation. The musts of Runs 3 and 6 are found to have a fruity aroma, absent in the musts of the other runs. The musts of Runs 5 and 6 are found to have more color than the musts of the other runs. The must of Run 4 is found to be the most blended and harmonious in flavor. The musts of Runs 3, 4, 5, and 6 are all found to have altered color, flavor and aroma characteristics as compared to the musts of Runs 1 and 2. Due to its harmonious and blended flavor characteristics, the must of Run 4 is found to be the most promising in its anticipated ability to develop into a high quality wine and is preferred by the taste panel over the remaining musts. The must of Run 3 is found by the taste panel to be the second most preferred must and the must of Run 6 is found to be the third most preferred must.

EXAMPLE V

A sample of the heat treated yeast of Example I is placed in a glass vial and stored in a refrigerator for a period of about six months. The sample is then removed from the refrigerator and employed in the fermentation process of Example I, comparing the fermentation activity of the heat treated and stored yeast with fresh untreated yeast. Similar results are obtained.

While the invention has been described in connection with certain presently preferred, illustrative embodiments, various modifications are contemplated for use in the practice of the present invention and will be apparent from this disclosure and the present practices in the fermentation art. Such modifications are intended to be within the scope of the appended claims except insofar as precluded by the prior art.

What is claimed is:

1. A method of treating previously dried yeast containing less than about 20% moisture, by weight, to increase its activity when used in fermentation processes which comprises the steps of: heating said previously dried, active dried yeast to a temperature in the range of about 30° C. to about 60° C.; and maintaining said yeast at about 30° C. to about 60° C. for at least 2 hours, whereby the resulting treated yeast exhibits increased activity when used in fermentation process.

2. A method of improving the color, flavor and aroma of a fermented alcoholic beverage formed in a fermentation process employing active dried yeast, comprising the steps of:

heating said previously dried active dried yeast containing less than about 20% moisture, by weight, to a temperature in the range of about 30° C. to about 60° C.;

maintaining said yeast at about 30° C. to about 60° C. for at least 2 hours; and then employing said treated active dried yeast in a fermentation process to produce a fermented alcoholic beverage; whereby said resulting fermented alcoholic beverage has improved color, flavor and aroma.

3. The method of claims 1 or 2 wherein the dried yeast is heated for about 3 to about 30 hours.

4. The method of claims 1 or 2 wherein the dried yeast is heated for about 4 to about 20 hours.

5. The method of claims 1 or 2 wherein the yeast is heated to a temperature of about 35° to about 55° C.

6. The method of claims 1 or 2 wherein the yeast is heated to a temperature of about 45° to about 55° C.

7. The method of claims 1 or 2 which further comprises employing the yeast in a fermentation mixture of a fermentation process after the yeast has been heated.

8. The method of claim 7 which further comprises subjecting the fermentation mixture to less than atmospheric pressures during the fermentation process.

9. The method of claim 2 wherein the alcoholic beverage is wine.

10. The active dried yeast products produced by the process of claim 1.

11. The product produced by the method of claim 3.

12. The product produced by the method of claim 4.

13. The product produced by the method of claim 5.

14. The product produced by the method of claim 6.

* * * * *